United States Patent [19]

Chun et al.

[11] Patent Number: 5,089,394

[45] Date of Patent: Feb. 18, 1992

[54] NEISSERIA DETECTION SYSTEM

[75] Inventors: Peter K. Chun, South San Francisco; Albert E. Chu, Hillsborough, both of Calif.

[73] Assignee: E-Y Laboratories, Inc., San Mateo, Calif.

[21] Appl. No.: 406,778

[22] Filed: Sep. 13, 1989

Related U.S. Application Data

[63] Continuation of Ser. No. 922,755, Oct. 24, 1986, abandoned, which is a continuation of Ser. No. 572,523, Jan. 20, 1984, abandoned, which is a continuation-in-part of Ser. No. 472,663, Mar. 7, 1983, abandoned, and a continuation-in-part of Ser. No. 472,664, Mar. 7, 1983, abandoned.

[51] Int. Cl.⁵ .................... C12Q 1/04; C12Q 1/54; C12Q 1/37; G01N 33/571
[52] U.S. Cl. .................... 435/34; 435/7.36; 435/7.2; 435/14; 435/24; 435/810; 435/871; 435/975; 436/827
[58] Field of Search ................ 435/4, 7, 14, 24, 34, 435/37, 39, 810, 871; 436/511, 800, 827

[56] References Cited

U.S. PATENT DOCUMENTS

| | | | |
|---|---|---|---|
| 3,862,011 | 1/1975 | Smith | 435/24 |
| 3,925,162 | 12/1975 | Kanno | 435/24 X |
| 4,115,543 | 9/1978 | Wallace et al. | 436/511 |
| 4,208,480 | 6/1980 | D'Amato et al. | 435/34 |
| 4,298,689 | 11/1981 | Doyle et al. | 435/34 |
| 4,308,348 | 12/1981 | Monget | 435/38 |

OTHER PUBLICATIONS

Curtis et al., "Br. J. Vener. Dis.", 57, (1981), pp. 253-255.
Eriquez et al., J. of Clin. Microbiol., vol. 18, Nov. 1983, pp. 1032-1039.
Arko et al., J. of Clin. Microbiol., vol. 9, No. 4, Apr. 1979, pp. 517-519.
D'Amato et al., J. of Clin. Microbiol., vol. 7, No. 1, Jan. 1978, pp. 77-81.
Chen et al., J. of Biological Chem., vol. 255, No. 4, Feb. 1980, pp. 1704-1710.
Eriquez et al., J. of Clin. Microbiol., vol. 12, No. 5, Nov. 1980, pp. 667-671.

Primary Examiner—Esther L. Kepplinger
Assistant Examiner—Toni Scheiner
Attorney, Agent, or Firm—Flehr, Hohbach, Test, Albritton & Herbert

[57] ABSTRACT

A specimen containing N. lactamica, N. meningitidis, N. gonorrhoeae or B. catarrhalis is incubated simultaneously with a first substrate for beta-galactosidase and a second substrate for gamma-glutamyl aminopeptidase to form reaction products with one or the other Neisseriae which yields a detectible first or second signal distinct from each other depending upon the presence of the enzyme. Signals may comprise distinct colors which emit either in the absence or presence of diazo dye coupler. A third substrate specific for prolyliminopeptidase in N. gonorrhoeae may be added to form a detectible third signal of the same type. The third substrate may be incubated simultaneously with the first two substrates or later. The absence of all of the first three signals is a positive indication that the specimen contains B. catarrhalis. Also, a diagnostic test kit for performing the above tests with or without lectin or antibody for agglutination based upon specific recognition.

20 Claims, No Drawings

NEISSERIA DETECTION SYSTEM

CROSS REFERENCE TO RELATED APPLICATIONS

This application is a continuation of application Ser. No. 922,755 filed Oct. 24, 1986, now abandoned, which is a continuation of application Ser. No. 572,523 filed Jan. 20, 1984, now abandoned, which is a continuation-in-part of copending U.S. applications Ser. No. 472,663 filed Mar. 7, 1983, now abandoned, and Ser. No. 472,664 filed Mar. 7, 1983, now abandoned.

BACKGROUND OF THE INVENTION

The present invention relates to the detection of one or more of four Neisseriae and Neisseriae-like organisms, namely *Neisseria lactamica* (*N. lactamica*), *Neisseria meningitidis* (*N. meningitidis*), *Neisseria gonorrhoeae* (*N. gonorrhoeae*), and *Branhamella catarrhalis* (*B. catarrhalis*).

Simple and rapid assays for Neisseria from biologically derived material (e.g., serum, urine, surface fluids, exudates, or from culture media or culture broth) are important tools in diagnosis. It is known that certain substrates are specifically reactive with enzymes in Neisseriae to change from a colorless to a colored form, or from one color to another upon incubation with such enzymes. [Zimmer, B. L., et al, *J. Clin. Microbiol.*, Vol. 10, p. 380 (1979)].

The aminopeptidase profiles of *N. gonorrhoeae* and *N. meningitidis* have been studied and reported to be differential and capable of being reproducibly determined using chromogenic substrates as set forth in Perrine, S., and Watson, R. R., *Abstracts of the Annual Meeting of the American Society for Microbiology*, p. 39 (1975). This reference discloses that the presence of a reaction product of a substrate for gamma-glutamyl aminopeptidase which does not react with the other pathogenic Neisseriae is a positive indication that the specimen contains *N. meningitidis*. Similarly, it is known that beta-galactosidase activity is an indication of the presence of *N. lactamica* and that a substrate o-nitrophenyl-D-galactopyranoside be employed to detect such activity [LeMinor, L. and Ben Hamida, F., *Ann. Inst. Pasteur*, 102:267 (1962)]. Also, it is known that *N. gonorrhoeae* contains prolyliminopeptidase enzyme so that a substrate specific for that enzyme could be employed as a marker for it. [Watson, R. R. and Perrine, S., 1978 in G. F. Brooks, E. C. Gotschlick, K. K. Holmes, W. D. Sawyer, and F. E. Young (eds.) *Immunobiology of Neisseria Gonorrhoeae*, ASM, Washington, D. C.]

SUMMARY OF THE INVENTION

It is a general object of the invention to provide a rapid and accurate test for the differential detection of suspected pathogenic Neisseriae.

Further objects and features of the invention will be apparent from the following description of its preferred embodiments.

In accordance with the above objects, a method has been provided for the detection in a single system of the known presence of one of the four pathogenic Neisseriae (*N. lactamica, N. gonorrhoeae, N. meningitidis,* and *B. catarrhalis*). The specimen is first incubated with a first substrate specific for beta-galactosidase in *N. lactamica* and with a second substrate specific for gamma-glutamyl aminopeptidase in *N. meningitidis* to form a reaction product between the first or second substrate and its corresponding Neisseria. Then a first or second signal is formed in response to detectible quantities of the first or second substrate reaction products. Preferable signals are visible colors or fluorescence at distinct wavelengths.

In a preferred embodiment, a third substrate specific for prolyliminopeptidase in *N. gonorrhoeae* is also simulanteously incubated to form a third signal in response to detectible quantities of such substrate. The absence of all three signals is an indication that the specimen probably contains *B. catarrhalis*, since *B. catarrhalis* lacks all the enzymes detected by the three substrates.

A diagnostic test kit is provided including the first and second substrates alone, or in combination with diazo dye color developers, if required. The diagnostic test kit may include the third substrate in admixture with the first two or may be isolated for a separate test. Additional confirmatory tests may be provided, including testing for surface N,N'-diacetylchitobiose forming a visible agglutination product. A preferred lectin comprises N,N'-diacetylchitobiose-specific lectin, e.g., succinylated wheat germ agglutinin. Another alternative test includes the addition to the test kit of a predetermined quantity of antibodies specific for only one of the Neisseriae to form an agglutination product in the presence of that Neisseria. A deagglutination product, DNA'ase, may be added to avoid autoagglutination of the Neisseria which could give a false positive in these confirmatory tests.

DETAILED DESCRIPTION OF THE PREFERRED EMBODIMENTS

In accordance with the present invention, a specimen suspected of containing any one of a number of bacteria is first screened to determine that it contains one of the four Neisseriae (*N. lactamica, N. meningitidis, N. gonorrhoeae,* and *B. catarrhalis*). This group of Neisseriae will be referred to herein as the pathogenic Neisseria. The prescreening is performed in a conventional manner. The microorganisms are first grown on a Thayer-Martin plate. Then a Gram stain and oxidase test are performed to determine that the microorganisms are Gram negative diplococci to yield a positive oxidase test. This is a presumptive indication that one of the pathogenic Neisseria is present.

A significant feature of the present invention is the selection of a particular sequence of substrates for specific enzymes in the Neisseria to form distinct signals such as color or fluorescence to provide a rapid test for diagnosis of the pathogens. In a preferred embodiment, such tests may be performed in a single tube or on a single absorbent solid surface of the type set forth in co-pending application Ser. No. 472,664.

After the above preliminary screening, the specimen is preferably mixed with three distinct substrates which ultimately yield distinct signals in response to the substrate reaction products. The substrates which are added include one which is specific for beta-galactosidase in *N. lactamica* (hereinafter, the first substrate), one which is specific for gamma-glutamyl aminopeptidase in N. meningitidis (hereinafter, the second substrate), and one specific for prolyliminopeptidase in *N. gonorrhoeae* (hereinafter the third substrate). In the overwhelming number of cases, only one of the four Neisseriae will be present. The presence of the reaction products of one of the above three substrates with its corresponding enzyme in the pathogenic Neisseria will produce one of the three colors. The absence of any color is a presumptive indication that the specimen includes only *B. catarrhalis*.

In one embodiment, the first and second signals comprise colors distinct from each other. Thus, for example, the substrate for the beta-galactosidase enzyme in *N. lactamica* may comprise the beta-D-galactoside derivatized with 5-bromo-3-chloro-indoyl (BCIG substrate). This yields a blue color.

Referring to the substrate for the gamma-glutamyl aminopeptidase in *N. meningitidis*, one suitable substrate is para-nitro-analide of gamma-glutamic acid. The color is yellow upon hydrolysis of the substrate.

In the above system, the signals produced by the reaction products of either the first or second substrates with their corresponding enzymes produce colors distinct from each other without the necessity of adding a diazo dye coupler. Thus, using the above specific substrates, the presence of blue reaction product indicates that *N. lactamica* is present while the presence of a yellow reaction product indicates that *N. meningitidis* is present. In those rare cases where both are present, a green color may develop.

In the above system, the third substrate (specific for *N. gonorrhoeae*) may be of a type which yields a colored reaction product only in the presence of diazo dye coupler. This is advantageous in the above test in that the third substrate may be present during the initial incubation but the diazo dye coupler may be added only if no color is produced during that incubation since lack of color is an indication that neither *N. lactamica* nor *N. meningitidis* are present. In that instance, the test is continued by the addition of an appropriate diazo dye coupler to produce a distinct color if *N. gonorrhoeae* is present. In one system of this type, a substrate for prolyliminopeptidase which only produces a color in the presence of the diazo dye coupler comprises proline-4-methoxy-2-napthylamide. This substrate or ones with other alkoxy substitutes for the methoxy group provide a very rapid reaction as set forth in co-pending application Ser. No. 472,664. Also as set forth therein, a suitable diazo dye coupler which may be added to the specimen after the lack of color after incubation is an o-aminoazotoluene diazonium salt (a dye known as Fast Garnet), which produces a red color in the presence of the reaction product of *N. gonorrhoeae* and its above substrate. If there is no color change after the addition of the diazo dye color, this generally indicates of the presence of *B. catarrhalis*.

In an analogue to the above system, fluorescent substrates which emit fluorescence at three distinct wavelengths in the presence of the above three enzymes in *N. lactamica*, *N. meningitidis*, or *N. gonorrhoeae*, respectively, may be employed. Since the wavelengths are distinct, the presence of the substrate-enzyme reaction products may be detected immediately after incubation with a fluorometer. A suitable fluorescent substrate for beta-galactosidase comprises 4-methyl-umbellifeyrl-beta-D-galactoside or fluoroscein-galactoside. Suitable fluorescent substrates for gamma-glutamyl aminopeptidase include gamma-glutamyl-4-methoxy-2-naphthylamide. Also a suitable fluorescent substrate for prolyliminopeptidase includes proline-4-methoxy2-naphthylamide.

The above test may be carried out in a solution in a well or test tube as is conventional in diagnostic testing. In the alternative, the test may be performed on an absorbent surface such as a cotton swab of the type described in Ser. No. 472,664, the disclosure of which is incorporated at this point by reference. One advantage of using the swab-type test is that the reactions have been found to be significantly faster than reaction of the solution of a well or test tube.

If an absorbent surface approach is utilized, the yellow color produced in the above reaction for *N. meningitidis* tends to be less distinct than the corresponding color produced in solution. Accordingly, in the presence of small quantities of *N. meningitidis* in the specimen, there may be a risk of failing to detect the yellow reaction product. In view of this, a particularly effective alternative test system for using with absorbent surfaces comprises a substrate for the gamma-glutamyl aminopeptidase which produces an intense color only in the presence of a diazo dye developer, suitable analogous to the substrate and developer for gonorrhoeae. Thus, for example, the substrate employed may be gamma-glutamyl-4-methoxy-2-naphthylamide and the corresponding Fast Garnet diazo dye coupler is added after incubation. In this instance, a red color is presumptive of the presence of *N. meningitidis*.

Since the same red color would be presumptive for the presence of *N. meningitidis* and *N. gonorrhoeae* in the test of the preceeding paragraph, a totally separate test is required for *N. gonorrhoeae*. In this instance, the substrate for *N. gonorrhoeae* is not added in the initial incubation stage, but is only added to a second portion of the specimen if no color is produced in the first stage which only includes the substrates for *N. lactamica* and *N. meningitidis*. In this test, only the substrate for *N. gonorrhoeae* is present in the test for the second specimen position (absorbent surface or in solution). Thus, if a red color is produced in the presence of this substrate, *N. gonorrhoeae* is present in the specimen. As with the other test, if no color is observed, either in the first specimen test (for *N. lactamica* or *N. meningitidis*) or in the second test (for *N. gonorrhoeae*), this is a presumptive indication of the presence of *B. catarrhalis*.

In instances where a positive test result is preferred for positive confirmation of *B. catarrhalis*, a substrate specific for phenylalanine aminopeptidase may be used. Phenylalanine aminopeptidase is only present in *B. catarrhalis* amongst the four organisms tested.

A confirmatory test may also be employed in combination with the above test. One type of confirmatory test would be the addition of a lectin of a type which reacts with N-acetylglucosamine or N,N'-diacetylchitobiose to form an agglutination product between the lectin and either of these substances as a positive indication that the specimen contains either *N. gonorrhoeae*, non-ecapsulated *N. meningitidis*, or both. A preferred lectin is wheat germ agglutinin and, more particularly, succinylated wheat germ agglutinin. As set forth in the aforementioned application Ser. No. 472,663, the lectin may be added along with the first substrate (for *N. lactamica*) and the second substrate (for *N. meningitidis*). If an agglutination product forms, this confirms the presence of *N. gonorrhoeae* or non-encapsulated *N. meningitidis*.

A confirmatory test analogous to the addition of lectin comprises the substitution of lectin with an antibody specific for *N. gonorrhoeae* (e.g., a polyclonal antibody commercially available from Pharmacia Diagnostic) or commercially available monoclonal or for one of the other pathogenic Neisseria to form a visible agglutination product. The antibody would be used in the same stage of the above test as the lectin. Thus, for example, it may be used in combination with the first, second and/or third substrates or in a separate confirmatory test.

When the lectin or antibody confirmation tests of the preceding paragraphs are used, it is desirable to include with the substrate mixture a reagent to reverse autoagglutination which may occur with certain strains of the above Neisseriae and create a false positive. One preferred reagent is crude or purified DNA'ase, or a preparation containing DNA'ase, at an effective concentration (e.g., 1 mg/ml).

The above lectin or *N. gonorrhoea* antibody tests may be used as a test for *N. gonorrhoea* in place of, rather than as confirmation of, the third substrate portion of the above test. This would be particularly advantageous in that at least two Neisseriae from a single culture plate [(1) *N. lactamica* or *N. meningitidis* and (2) *N. gonorrhoea*] may be identified in a single test.

A diagnostic test kit suitable for the detection of the above Neisseriae after screening includes a first substrate specific for beta-galactosidase in *N. lactamica* and capable of forming a first detectible signal in the presence of beta-galactosidase and a second substrate specific for beta-glutamyl aminopeptidase in *N. meningitidis* and capable of forming a second detectible signal in the presence of a beta-galactosidase, distinct from the first signal. Such first and second substrates may comprise compounds which form visible distinct colors in the presence of the corresponding enzymes by themselves without the necessity of utilizing diazo dye color developers or may be of a type which require such color developers. In the latter instance, the appropriate diazo dye color developers would be included with the test kit.

It is preferable that the first and second substrates set forth above be used in combination with each other in a first, simultaneous test.

Accordingly, such substrates may be add mixed in the test kit or, if desired for some reason, packaged separately and mixed by the user of the kit. If diazo dye color developers are required, it is preferable that they be packaged separately in the kit because their presence may interfere with reaction of the substrate and enzyme in the Neisseria.

The diagnostic test kit preferably also includes a third substrate, one specific for prolyliminopeptidase in *N. gonorrhoeae* and capable of forming a detectible signal in the presence of of prolyliminopeptidase. In an analogous manner to the foregoing, if the third substrate requires development by coupling to a diazo color to emit a color, the test kit should also include such diazo dye developer. The third substrate may be in admixture with the first two substrates in the test kit or may be mixed with them by the user, if simultaneous development of all three substrates is to be performed. If, for reasons set forth above with respect to absorbent surface substrates, it is desirable to utilize these same diazo dye coupler for the *N. meningitidis* and *N. gonorrhoeae* enzymes, then the test for *N. gonorrhoeae* is performed separately (on a separate absorbent surface or separate container in the kit). Also, all three substrates may be premixed in the test kit by use of different colors for each substrate.

The test kit may include one or more agglutinating reagents for confirmatory or independent testing. Thus, the test kit may also include a predetermined quantity of antibody specifically for only one of the Neisseria (e.g., *N. gonorrhoeae*) in sufficient quantity to form a visible agglutination product in the presence of the one Neisseriae. The antibody may be packaged separately or in admixture with the first and/or second and/or third substrates. For the reasons set forth above, it is preferable to include a Neisseria deagglutination reagent when an agglutination test is performed.

By way of analogy to the presence of the antibody, the substrate container of the diagnostic test kit may also include a predetermined quantity of lectin of a type which reacts with N-acetylglucosamine or N,N'-diacetylchitobiose to form a visible agglutination product. One such lectin is wheat germ agglutinin. To avoid false positives due to autoagglutination of the Neisseria, an appropriate deaggultination agent, such as DNA'ase, may also be included in the container.

Where the diagnostic test kit is to be used for testing in solution, it is advantageous to include in the kit a plate with appropriately labeled well with the aforementioned reagents in dry form already present in the wells so that the user only need add the specimen to the wells. In the alternative, if the test is to be performed utilizing absorbent surfaces, such as swabs, it is preferable to include the appropriate reagents previously impregnated into the absorbent surface and dried for shipment. In this instance, the user only need contact the absorbent surface with the specimen to perform the test. The above diagnostic test kits have been described with respect to color producing substrates. It is to be understood that in accordance with principles set forth above, such color producers may be substituted with substrates which produce fluorescence at wavelengths distinct from each other.

The following examples are illustrative of the present invention. In each instance, the specimen is prescreened for the presence of pathogenic Neisseriae by growth of the microorganims on selective media, such as Thayer-Martin culture medium. A Gram stain and oxidase test are performed as a positive indication that the microorganisms are Gram negative type diplococci, giving a positive oxidase test. This combination of prescreening is a presumptive indication of the presence of one of the four pathogenic Neiserriae.

EXAMPLE 1

In this example, substrates for *N. lactamica* and *N. meningitidis* are added which are color producing in the absence of color developers while the third substrate is present for *N. gonorrhoeae*, which requires the presence of a developer.

In a tube or well, 50 microliters of each of the following reagents are added in a phosphate buffered solution: bromochloro-indoyl beta-D-galactoside (1 mg/ml), gamma-glutamyl-paranitroanilide (1 mg/ml) and proline-4-methoxy-2-naphthylamide (1 mg/ml). In addition, wheat germ agglutinate is present in a concentration of 1 mg/ml together with DNA'ase. Then, the specimen (10 large colonies from the culture plate) was added to the wells. The mixture is incubated for 30 minutes at 37° C. A blue color is confirmative of the presence of *N. lactamica*, while a yellow color is confirmative of the presence of *N. meningitidis*.

If no color is produced after incubation, an appropriate diazo dye coupler (Fast Garnet) is added in a solution of 0.2 mg/ml of water. The production of a red color in the presence of the developer is confirmative of the presence of *N. gonorrhoeae*. If there is no color change, this is presumptive of the presence of *B. catarrhalis*.

A visible agglutination product indicates the presence of N. meningitidis or N. gonorrhoeae as a confirmatory test of the above procedure. As set forth above, an appropriate antibody (monoclonal or polyclonal) may be substituted for the lectin in this test.

EXAMPLE 2

In this procedure, 50 microliters of a solution of 5-bromo-3-chloro-indoyl beta-D-galactosidase (1 mg/ml) is mixed with gamma-glutamyl-4-methoxy-2-naphthylamide (1 mg/ml) in phosphate buffered saline. Then, a specimen as in Example 1 is added.

As with the test of Example 1, a blue color is indicative of the presence of N. lactamica. If there is no color, an appropriate diazo dye coupler is added such as Fast Garnet (0.2 mg/ml). If a red color is produced, this indicates the presence of N. meningitidis.

If no color is produced in the above test, a second test may be performed in which the only substrate added is proline-4-methoxy-2-naphthylamide (1 mg/ml) in phosphate buffered saline. After incubation, an appropriate diazo dye coupler (Fast Garnet) is added at a concentration of 0.2 mg/ml. If a red color develops, this indicates the presence of N. gonorrhoeae. If no color develops in either of the above two tests, this is presumptive of the presence of B. catarrhalis.

EXAMPLE 3

The general test procedure of Example 1 was followed with the exception that fluorescent substrates were substituted for a chromogenic substrates of Example 1. Here 50 micrograms of a phosphate buffered saline solution is employed including the following three substrates (a) 4-methyl-umbelliferyl-beta-D-galactisidase, (b) gamma-glutamyl-4-methoxy-2-naphthylamide, and (c) proline-aminomethylcoumarin (all at concentrations of 1 mg/ml).

Fluorescence emitting at a wavelength of 450 nm indicates the presence of N. lactamica; fluorescence emitting at a wavelength of 425 nm indicates the presence of N. meningitidis, and fluorescence emitting at a wavelength of 460 nm indicates the presence of N. gonorrhoeae. If no fluorescence is emitted at the above three wavelengths, this indicates the presence of B. catarrhalis.

Further tests can be performed to confirm B. catarrhalis by using phenylalanyl-4-methoxy-2-naphthalamide.

What is claimed is:

1. A method for the detection of a Neisseria in a biologically derived specimen including a Neisseria selected from the group consisting of N. lactamica, N. meningitidis, N. gonorrhoea, and B. catarrhalis, said specimen having been prescreened so that it presumptively contains no Neisseria other than ones in said group, said method comprising the steps of
    (a) simultaneously incubating the specimen with (1) a first substrate specific for betagalactosidase in N. lactamica, but not specific for gamma-glutamyl aminopeptidase, to form a betagalactosidase reaction product with said first substrate, if N. lactamica is present in the specimen, (2) a second substrate specific for gamma-glutamyl aminopeptidase in N. meningitidis, but not specific for betagalactosidase, to form a gamma-glutamyl aminopeptidase reaction product with said second substrate, if N. meningitidis is present in the specimen, and (3) a third substrate specific for prolyliminopeptidase capable of forming a prolyliminopeptidase reaction product with said third substrate, if prolyliminopeptidase is present in the specimen, said prolyliminopeptidase reaction product being undetectable, (b) forming detectable first or second signals distinct from each other in response to the presence of detectable quantities of said N. lactamica or N. meningitidis reaction products, respectively, as presumptive evidence of the presence of N. lactamica or N. meningitidis in the specimen,
    (c) detecting said first or second signals, if formed,
    (d) if neither said first nor second signals are formed in step (c), adding a signal producing reagent capable of reacting with said prolyliminopeptidase reaction product to form a detectable third signal, as presumptive evidence of the presence of N. gonorrhoea in the specimen, the absence of said detectable third signal being presumptive evidence of the presence of B. catarrhalis in the specimen, and
    (e) then detecting said third signal.

2. The method of claim 1 in which said first and second signals comprise distinct first and second visible colors.

3. The method of claim 2 in which said first reaction product emits said first color in the absence of a diazo dye coupler.

4. The method of claim 2 together with a step of coupling said first reaction product with a diazo dye coupler to form said first color.

5. The method of claim 2 in which said second reaction product emits said second color in the absence of a diazo dye coupler.

6. The method of claim 2 together with a step of coupling said second reaction product with a diazo dye coupler to form said second color.

7. The method of claim 1 in which said first and second signals comprise fluorescence which emits at first and second wavelengths distinct from each other.

8. The method of claim 1 in which said first and second signals comprise colors distinct from each other which are visible in the absence of a diazo dye coupler.

9. The method of claim 1 in which said signal producing reagent comprises a diazo dye coupler.

10. The method of claim 1 in which a predetermined quantity of antibody specific for N. gonorrhoea is added in step (a) in sufficient quantity to form a visible agglutination product if the N. gonorrhoea is present.

11. The method of claim 1 in which a predetermined quantity of lectin, of a type which reacts with N-acetylglucosamine or N,N'-diacetylchitobiose if N-acetylglucosamine or N,N'-diacetylchitobiose are present in the specimen, is added in step (a) and an agglutination product between the lectin and either N-acetylglucosamine or N,N'-diacetylchitobiose in the specimen is detected as a positive indication that the specimen contains either N. gonorrhoea, N. meningitidis, or both.

12. The method of claim 11 in which the lectin comprises wheat germ agglutinin.

13. The method of claim 11 in which an agent which reverses the mechanism of autoagglutination of Neisseria in the specimen is added in step (a).

14. The method of claim 13 in which said agent is DNA'ase.

15. A diagnostic test kit for the detection of a Neisseria in a biologically derived specimen including a Neisseria selected from the group consisting of N. lactamica, N. meningitidis, N. gonorrhoea, and B. catarrhalis, said test kit comprising (a) a reaction container,
(b) a first substrate specific for betagalactosidase and capable of exhibiting a first visible color by itself without a diazo dye coupler in the presence of beta-galactosidase,
(c) a second substrate specific for gamma-glutamyl aminopeptidase and capable of exhibiting a second visible color by itself without a diazo dye coupler in the presence of gamma-glutamyl aminopeptidase, distinct from said first color,
(d) a third substrate specific for prolyliminopeptidase and capable of forming a detectable color in the presence of prolyliminopeptidase only in the presence of a diazo dye coupler to exhibit a color, and
(e) a diazo dye coupler for the reaction product of said third substrate and prolyliminopeptidase.

16. The diagnostic test kit of claim 15 including a predetermined quantity of antibody specific for only one of said Neisseria in sufficient quantity to form a visible agglutination product in the presence of said one Neisseria.

17. The diagnostic test kit of claim 15 including a predetermined quantity of lectin of a type which reacts with N-acetylglucosamine or N,N'-diacetylchitobiose to form a visible agglutination product.

18. The diagnostic test kit claim 17 in which the lectin comprises wheat germ agglutinin.

19. The diagnostic test kit of claim 15 together with a biochemical agent which reverses the mechanism of autoagglutination in Neisseria.

20. The diagnostic test kit of claim 19 in which said biochemical agent is DNA'ase.

* * * * *